United States Patent
Heikenfeld (10) Patent No.: US 10,932,761 B2
(45) Date of Patent: Mar. 2, 2021

(54) ADVANCED SWEAT SENSOR ADHESION, SEALING, AND FLUIDIC STRATEGIES

(71) Applicant: University Of Cincinnati, Cincinnati, OH (US)

(72) Inventor: Jason C. Heikenfeld, Cincinnati, OH (US)

(73) Assignee: University of Cincinnati, Cincinnati, OH (US)

(*) Notice: Subject to any disclaimer, the term of this patent is extended or adjusted under 35 U.S.C. 154(b) by 134 days.

(21) Appl. No.: 15/314,412

(22) PCT Filed: May 28, 2015

(86) PCT No.: PCT/US2015/032843
§ 371 (c)(1),
(2) Date: Nov. 28, 2016

(87) PCT Pub. No.: WO2015/184072
PCT Pub. Date: Dec. 3, 2015

(65) Prior Publication Data
US 2017/0100102 A1 Apr. 13, 2017

Related U.S. Application Data

(60) Provisional application No. 62/115,851, filed on Feb. 13, 2015, provisional application No. 62/114,835, (Continued)

(51) Int. Cl.
*A61B 10/00* (2006.01)
*A61N 1/32* (2006.01)
(Continued)

(52) U.S. Cl.
CPC ........ *A61B 10/0064* (2013.01); *A61B 5/0531* (2013.01); *A61B 5/14517* (2013.01);
(Continued)

(58) Field of Classification Search
CPC .......... A61B 10/0064; A61B 10/14517; A61B 5/14517
See application file for complete search history.

(56) References Cited

U.S. PATENT DOCUMENTS

| 4,190,060 A | 2/1980 | Greenleaf et al. |
| 4,542,751 A | 9/1985 | Webster et al. |
| (Continued) | | |

FOREIGN PATENT DOCUMENTS

| CA | 2869469 A1 | 10/2013 |
| CN | 101489470 A | 7/2009 |
| (Continued) | | |

OTHER PUBLICATIONS

European Patent Office, Official Communication for EP Application No. 13 718 933.8-1101 dated Feb. 14, 2018 (5 pages).
(Continued)

*Primary Examiner* — Puya Agahi
(74) *Attorney, Agent, or Firm* — Wood Herron & Evans LLP (57) ABSTRACT

A sweat sensor device (200) includes one or more sweat sensors (220) and a seal (280) covering the one or more sweat sensors (220). The seal (280) is adapted to protect the sweat sensors (220) from outside contaminants when the device (200) is placed on the skin (12). The sweat sensor device (200) may include an absorbing medium (230) to absorb sweat from the skin (12) that is covered by the seal (280). The seal (280) can be permeable to gas, permeable to water and impermeable to at least one aqueous solute, or selectively permeable to at least one aqueous solute. The sweat sensor device (200) may include an artificial sweat stimulation mechanism (345) for stimulating sweat when the device (200) is placed on the skin (12).

18 Claims, 3 Drawing Sheets

Related U.S. Application Data filed on Feb. 11, 2015, provisional application No. 62/003,675, filed on May 28, 2014.

(51) Int. Cl.
| | |
|---|---|
| *A61N 1/04* | (2006.01) |
| *A61B 5/145* | (2006.01) |
| *A61B 5/00* | (2006.01) |
| *A61B 5/0531* | (2021.01) |
| *A61B 5/053* | (2021.01) |

(52) U.S. Cl.
CPC ........ *A61B 5/14521* (2013.01); *A61B 5/4266* (2013.01); *A61B 5/6833* (2013.01); *A61N 1/0428* (2013.01); *A61N 1/325* (2013.01); *A61B 5/053* (2013.01); *A61B 2010/0009* (2013.01); *A61B 2503/045* (2013.01); *A61B 2503/10* (2013.01); *A61B 2503/12* (2013.01); *A61B 2560/0412* (2013.01); *A61B 2560/0443* (2013.01); *A61B 2562/18* (2013.01)

(56) References Cited

U.S. PATENT DOCUMENTS

| | | | |
|---|---|---|---|
| 4,756,314 | A | 7/1988 | Eckenhoff et al. |
| 4,820,263 | A | 4/1989 | Spevak et al. |
| 5,036,861 | A | 8/1991 | Sembrowich et al. |
| 5,050,604 | A | 9/1991 | Reshef et al. |
| 5,140,985 | A | 8/1992 | Schroeder et al. |
| 5,246,003 | A | 9/1993 | DeLonzor |
| 5,438,984 | A | 8/1995 | Schoendorfer |
| 5,441,048 | A * | 8/1995 | Schoendorfer .... A61B 5/14521 600/346 |
| 5,556,789 | A | 9/1996 | Goerlach-Graw et al. |
| 5,814,599 | A | 9/1998 | Mitragotri et al. |
| 5,944,662 | A | 8/1999 | Schoendorfer |
| 6,198,953 | B1 | 3/2001 | Webster et al. |
| 6,256,533 | B1 | 7/2001 | Yuzhakov et al. |
| 6,269,265 | B1 | 7/2001 | Anderson |
| 6,299,578 | B1 | 10/2001 | Kurnik et al. |
| 6,592,529 | B2 | 7/2003 | Marett |
| 6,666,821 | B2 | 12/2003 | Keimel |
| 7,190,986 | B1 | 3/2007 | Hannula et al. |
| 7,219,534 | B2 | 5/2007 | Campbell |
| 7,378,054 | B2 | 5/2008 | Karmali |
| 7,383,072 | B2 | 6/2008 | Edmonson et al. |
| 7,384,396 | B2 | 6/2008 | Samuels et al. |
| 7,749,445 | B2 | 7/2010 | Masters |
| 7,813,780 | B2 | 10/2010 | Shah et al. |
| 7,842,234 | B2 | 11/2010 | Lauks et al. |
| 7,959,791 | B2 | 6/2011 | Kjaer et al. |
| 8,125,539 | B2 | 2/2012 | Takashima |
| 8,128,889 | B2 | 3/2012 | Fujimoto et al. |
| 8,252,248 | B2 | 8/2012 | Kramer |
| 8,391,946 | B2 | 3/2013 | Sugenoya et al. |
| 8,565,850 | B2 | 10/2013 | Martinsen et al. |
| 8,593,287 | B2 | 11/2013 | Hayter et al. |
| 8,617,067 | B2 | 12/2013 | Jain et al. |
| 9,133,024 | B2 | 9/2015 | Phan et al. |
| 9,918,671 | B2 * | 3/2018 | Macaluso ............ A61B 5/6833 |
| 2002/0091312 | A1 | 7/2002 | Berner et al. |
| 2003/0135100 | A1 | 7/2003 | Kim et al. |
| 2003/0191376 | A1 | 10/2003 | Samuels et al. |
| 2003/0201194 | A1 | 10/2003 | Heller et al. |
| 2004/0249310 | A1 | 12/2004 | Shartle et al. |
| 2004/0267189 | A1 | 12/2004 | Mavor et al. |
| 2005/0069925 | A1 | 3/2005 | Ford et al. |
| 2005/0106713 | A1 | 5/2005 | Phan et al. |
| 2005/0177035 | A1 | 8/2005 | Botvinick et al. |
| 2005/0192528 | A1 | 9/2005 | Tapper |
| 2005/0197554 | A1 | 9/2005 | Polcha |
| 2006/0004271 | A1 | 1/2006 | Peyser et al. |
| 2006/0062852 | A1 | 3/2006 | Holmes |
| 2006/0127964 | A1 | 6/2006 | Ford et al. |
| 2006/0253011 | A1 | 11/2006 | Edmonson et al. |
| 2006/0254341 | A1 | 11/2006 | Campbell |
| 2007/0027383 | A1 | 2/2007 | Peyser et al. |
| 2007/0032731 | A1 | 2/2007 | Lovejoy et al. |
| 2007/0179371 | A1 | 8/2007 | Peyser et al. |
| 2008/0015494 | A1 | 1/2008 | Santini et al. |
| 2008/0045816 | A1 | 2/2008 | Jang et al. |
| 2008/0154179 | A1 | 6/2008 | Cantor |
| 2008/0286349 | A1 | 11/2008 | Nomoto et al. |
| 2008/0306362 | A1 | 12/2008 | Davis |
| 2009/0076345 | A1 | 3/2009 | Manicka et al. |
| 2009/0204008 | A1 | 8/2009 | Beilin |
| 2009/0270704 | A1 | 10/2009 | Peyser et al. |
| 2010/0044224 | A1 | 2/2010 | Kataky |
| 2010/0063372 | A1 | 3/2010 | Potts et al. |
| 2010/0130843 | A1 | 5/2010 | Caceres Galvez et al. |
| 2010/0132485 | A1 | 6/2010 | Erez et al. |
| 2010/0198521 | A1 | 8/2010 | Haick |
| 2011/0079521 | A1 | 4/2011 | Revol-Cavalier |
| 2011/0118656 | A1 | 5/2011 | Eckhoff et al. |
| 2011/0152718 | A1 * | 6/2011 | Revol-Cavalier .... A61B 5/4266 600/573 |
| 2011/0178380 | A1 | 7/2011 | Chowdhury |
| 2011/0196283 | A1 | 8/2011 | Imran et al. |
| 2011/0208458 | A1 | 8/2011 | Pinter et al. |
| 2011/0275918 | A1 | 11/2011 | Yamashita et al. |
| 2012/0004570 | A1 | 1/2012 | Shimizu et al. |
| 2012/0028283 | A1 | 2/2012 | Hoss et al. |
| 2012/0123220 | A1 | 5/2012 | Iyer et al. |
| 2012/0165626 | A1 | 6/2012 | Irina et al. |
| 2012/0209226 | A1 | 8/2012 | Simmons et al. |
| 2012/0229661 | A1 | 9/2012 | Sekiguchi et al. |
| 2012/0277697 | A1 | 11/2012 | Haghooie |
| 2012/0285829 | A1 | 11/2012 | Mount et al. |
| 2012/0317430 | A1 | 12/2012 | Rahman et al. |
| 2012/0323097 | A9 | 12/2012 | Chowdhury |
| 2013/0006079 | A1 | 1/2013 | Feldman et al. |
| 2013/0010108 | A1 | 1/2013 | Hashizume et al. |
| 2013/0013028 | A1 | 1/2013 | Kriksunov et al. |
| 2013/0053668 | A1 | 2/2013 | Lin |
| 2013/0079605 | A1 | 3/2013 | Bandaru et al. |
| 2013/0099937 | A1 | 4/2013 | Azimi |
| 2013/0108667 | A1 | 5/2013 | Soikum et al. |
| 2013/0123595 | A1 | 5/2013 | Currie et al. |
| 2013/0183399 | A1 | 7/2013 | Blow et al. |
| 2013/0306491 | A1 | 11/2013 | Briman et al. |
| 2013/0317333 | A1 | 11/2013 | Yang et al. |
| 2014/0012114 | A1 | 1/2014 | Zevenbergen et al. |
| 2014/0025000 | A1 | 1/2014 | Currie et al. |
| 2014/0206977 | A1 | 7/2014 | Bahney et al. |
| 2014/0275862 | A1 | 9/2014 | Kennedy |
| 2014/0276220 | A1 | 9/2014 | Briscoe et al. |
| 2014/0343371 | A1 | 11/2014 | Sowers, II et al. |
| 2015/0057515 | A1 | 2/2015 | Hagen et al. |
| 2015/0112164 | A1 | 4/2015 | Heikenfeld et al. |
| 2015/0112165 | A1 | 4/2015 | Heikenfeld |
| 2016/0058354 | A1 | 3/2016 | Phan et al. |
| 2016/0066828 | A1 | 3/2016 | Phan et al. |
| 2016/0157768 | A1 | 6/2016 | Braig et al. |

FOREIGN PATENT DOCUMENTS

| | | |
|---|---|---|
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |

(56) References Cited

FOREIGN PATENT DOCUMENTS

| WO | 2006133101 A2 | 12/2006 |
|---|---|---|
| WO | 2007097754 A1 | 8/2007 |
| WO | 2007146047 A1 | 12/2007 |
| WO | 2008082687 A1 | 7/2008 |
| WO | 2008095940 A1 | 8/2008 |
| WO | 2009004001 A1 | 1/2009 |
| WO | 2009052321 A2 | 4/2009 |
| WO | 2010/017578 A1 | 2/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |

OTHER PUBLICATIONS

European Patent Office, Extended European Search Report issued in European Application No. 15819306.0-1115 dated Feb. 9, 2018 (9 pages).
International Searching Authority, Search Report and Written Opinion issued in International Application No. PCT/US2017/067495 dated Mar. 1, 2018, 10 pages.
International Searching Authority/US, International Search Report and Written Opinion issued in corresponding PCT Application No. PCT/US2016/059392, dated Feb. 15, 2017 (12 pages).
European Patent Office, Extended Search Report issued in European Application No. 15844313.5 dated Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
European Patent Office, Extended European Search Report issued for European Patent Application No. 15800043.0, dated Apr. 16, 2018, 11 pages.
European Patent Office, Supplemental European Search Report issued in European Application No. 15799514.3-1657 dated Dec. 7, 2017, 8 pages.
European Patent Office, Supplemental European Search Report issued in European Application No. 15799317.1-1657 dated Dec. 21, 2017, 9 pages.
European Patent Office, Partial European Search Report issued in European Application No. 15800043.0-115 dated Jan. 8, 2018, 13 pages.
International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Sonner, Z., et al., "The microfluidics of the eccrine sweat gland, including biomarker partitioning, transport, and biosensing implications,"Biomicrofluidics, vol. 9, pp. 031301-1-031301-19, CrossMark, 19 pages.
International Searching Authority, Search Report and Written Opinion issued in related International Application No. PCT/US2017/013453 dated May 18, 2017, 14 pages.
International Searching Authority, Search Report and Written Opinion issued in related International Application No. PCT/US2017/039421 dated Sep. 6, 2017, 10 pages.
International Searching Authority, Search Report and Written Opinion issued in related International Application No. PCT/US2017/040588 dated Sep. 25, 2017, 11 pages.
Australian Patent Office, Patent Examination Report No. 1 issued in Australian Application No. 2013243541 dated Nov. 25, 2016, 4 pages.
Australian Patent Office, Notice of Acceptance for Patent Application issued in Australian Application No. 2013243541 dated Mar. 23, 2017 (3 pages).
Chinese Patent Office, First Office Action issued in Chinese Application No. 201380028053.8 dated Dec. 21, 2015, 4 pages.
Chinese Patent Office, Second Office Action issued in Chinese Application No. 201380028053.8 dated Sep. 20, 2016, 8 pages (including English language translation).
Chinese Patent Office, Third Office Action issued in Chinese Application No. 201380028053.8 dated Mar. 20, 2017, 17 pages (including English language translation).
European Patent Office, Written Opinion of the International Searching Authority / International Preliminary Report on Patentability dated Oct. 16, 2014 (14 pages).
European Patent Office, Partial European Search Report issued in European Application No. 16203346.8-1657 dated Mar. 24, 2017, 7 pages.
Fu et al., "Controlled Reagent Transport in Disposable 2D Paper Networks", The Royal Society of Chemistry 2010, Lab Chip, 2010, 10, 918-920.
International Bureau, Notification Concerning Transmittal of International Preliminary Report on Patentability issued in International Application No. PCT/US13/35092 dated Oct. 7, 2014, 14 pages.
International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.
International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.
International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.
International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.
International Searching Authority, Search Report and Written Opinion in International Application No. PCT/US2016/061098 dated Dec. 19, 2014, 13 pages.
International Searching Authority, Search Report and Written Opinion issued in International Application No. PCT/US2014/061083 dated Mar. 31, 2015, 18 pages.
International Searching Authority, Search Report and Written Opinion issued in International Application No. PCT/US2015/032830 dated Aug. 14, 2015, 9 pages.

(56) References Cited

OTHER PUBLICATIONS

International Searching Authority, Search Report and Written Opinion issued in International Application No. PCT/US2015/032843 dated Oct. 26, 2015, 11 pages.
International Searching Authority, Search Report and Written Opinion issued in International Application No. PCT/US2015/032893 dated Nov. 13, 2015, 14 pages.
International Searching Authority, Search Report and Written Opinion issued in International Application No. PCT/US2015/032866 dated Nov. 19, 2015, 12 pages.
International Searching Authority, Search Report and Written Opinion issued in International Application No. PCT/US2015/051439 dated Dec. 28, 2015, 7 pages.
International Searching Authority, Search Report and Written Opinion issued in International Application No. PCT/US2015/040113 dated Feb. 4, 2016, 13 pages.
International Searching Authority, Search Report and Written Opinion issued in International Application No. PCT/US16/18635 dated May 6, 2016, 12 pages.
International Searching Authority, Search Report and Written Opinion issued in International Application No. PCT/US16/17726 dated May 12, 2016, 9 pages.
International Searching Authority, Search Report and Written Opinion issued in International Application No. PCT/US16/50928 dated Sep. 9, 2016, 8 pages.
International Searching Authority, Search Report and Written Opinion issued in International Application No. PCT/US16/43862 dated Oct. 19, 2016, 14 pages.
International Searching Authority, Search Report and Written Opinion issued in International Application No. PCT/US16/59392 dated Oct. 28, 2016, 13 pages.
Japanese Patent Office, Office Action issued in Japanese Application No. 2015-504702 dated Jan. 20, 2017, 7 pages (including English language translation).
Stoppa, Matteo, et. al., "Wearable Electronics and Smart Tectiles: A Critical Review," Sensors, 2014, pp. 11957-11992, vol. 14 (36 pages).

* cited by examiner

ADVANCED SWEAT SENSOR ADHESION, SEALING, AND FLUIDIC STRATEGIES

CROSS-REFERENCE TO RELATED APPLICATIONS

This application claims the benefit of U.S. Provisional Applications No. 62/003,675, filed on May 28, 2014, No. 62/114,835, filed on Feb. 11, 2015, and No. 62/115,851, filed on Feb. 13, 2015, the disclosures of which are hereby incorporated by reference herein in their entirety.

BACKGROUND OF THE INVENTION

Sweat sensing technologies have enormous potential for applications ranging from athletics, to neonates, to pharmacological monitoring, and to personal digital health, to name a few applications. Sweat contains many of the same biomarkers, chemicals, or solutes that are carried in blood and can provide significant information enabling one to diagnose ailments, health status, toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of medical literature utilizes the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet succeeded to produce viable commercial products, reducing the publically perceived capability and opportunity space for sweat sensing.

Furthermore, existing approaches lack advanced adhesion, sealing, and fluidic strategies for sweat sensing materials, devices, and systems. For example, externally exposed devices have been demonstrated on skin but which could not be used by a swimmer, or used for high resolution chronological monitoring of biomarkers if placed in an area where 'older sweat' could contact the device. Sensors on skin have also been demonstrated in the lab, but only the sensors and not with the integrated and sealed electronics needed for real-world use. In summary, much of the prior art teaches interesting basic scientific demonstrations, but such devices severely lack the inventive steps and elements to enable high-performance, ergonomic, fail-proof, and compelling sweat sensing.

SUMMARY OF THE INVENTION

Many of the drawbacks stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. With such a new invention, sweat sensing could become a compelling new paradigm as a biosensing platform.

The present invention provides sweat sensor device with advanced sweat sensor adhesion, sealing, and fluidic strategies. In one embodiment, a sweat sensor device includes one or more sweat sensors and a seal covering said one or more sweat sensors, said seal for protecting said sweat sensors from outside contaminants when said device is placed on skin.

In one embodiment, a sweat sensor device includes one or more sweat sensors and a membrane between said sweat sensor and skin. Said membrane is effective to selectively transport one or more solutes from said sweat to said sweat sensor when the device is placed on the skin.

The objects and advantages of the present invention will be further appreciated in light of the following detailed descriptions and drawings.

DETAILED DESCRIPTION OF THE INVENTION

Figure 1A:
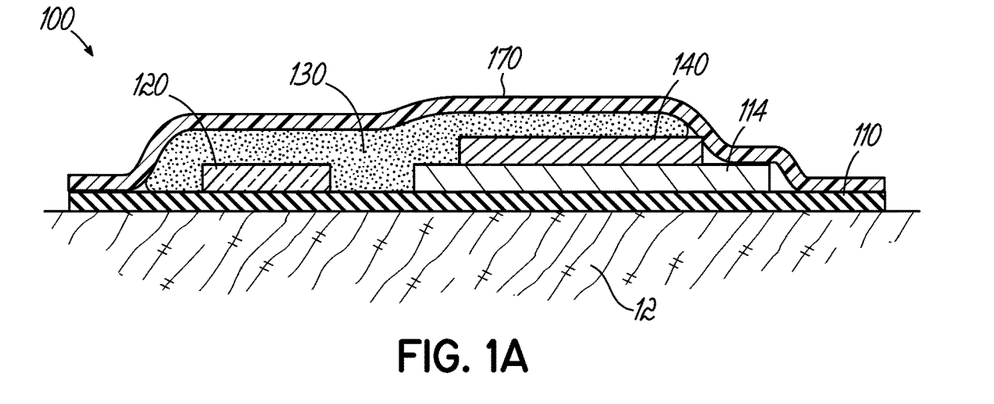
FIG. 1A is a cross-sectional view of a sealed device according to one embodiment of the present invention.

With reference to FIG. 1A, in one embodiment of the present invention a sweat sensor device 100 is placed onto skin 12 by virtue of an adhesive 110. Adhesive 110 is porous or permeable to sweat or solutes in sweat. In other embodiments, adhesives can be electrically conductive, insulating, permeable, impermeable, or have other various properties. Exemplary adhesives useful in the present invention are manufactured by 3M Corp. Device 100 further includes a substrate 114 that carries electronics 140. In one embodiment, the substrate 114 is a Kapton film. Electronics 140 may include, for example, such components as an electronics controller, communication circuit, memory, microcontrollers, antennas, and other electronics useful in wearable sensors. Device 100 further includes one or more sensors 120 for sensing sweat, sweat solutes, skin impedance, biomarkers, or combinations thereof. Sensors 120 may be connected to electronics 140, as discussed further below. Embodiments of the present invention may include one or more sensors that may be of similar or different types. For instance, in one embodiment, a device may include a sensor for sensing sweat solutes and an impedance sensor. Device 100 includes an absorbent medium 130, which may absorb sweat when the device 100 is sensing sweat. In the illustrated embodiment, the absorbent medium 130 is in contact with the sensor 120 and electronics 140. By way of example, the absorbent medium 130 may be a textile, a desiccant, or a swelling hydrogel. The device 100 includes a seal 170 that covers the other components of device 100. By way of example, seal 170 could be a stretchable expandable film, such as one made of vinylidene chloride or plastic paraffin. The seal 170 is impervious to vapor or fluids and forms a seal between the device 100 and the skin. The seal 170 advantageously aids in protecting the device 100 from outside contaminants. The seal between the device 100 and the skin 12 may be formed, for example, by both the seal 170 and a function of the adhesive 110, or through any other suitable mechanism such as applied pressure. In the illustrated embodiment, seal 170 and the adhesive 110 together seal the device 100 to the skin 12. Aspects of sweat sensing and sweat sensors are further discussed in PCT/US2013/035092, filed Apr. 3, 2013, the disclosure of which is hereby incorporated herein by reference in its entirety.

Figure 1B:
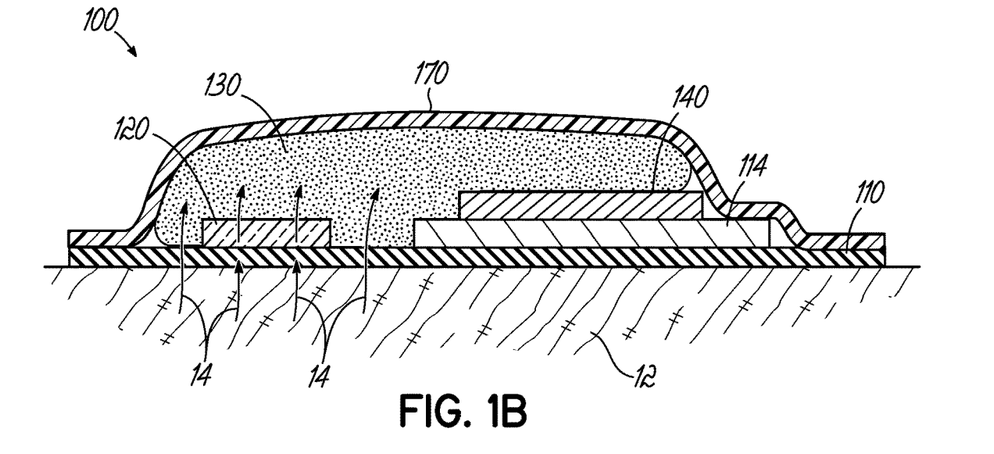
FIG. 1B is a cross-sectional view of the sealed device of FIG. 1A after the device has begun sensing sweat.

With reference to FIG. 1B, a flow 14 of sweat from the skin 12 is measured by the sensor 120, and the sweat flows into the absorbent medium 130. As shown in FIG. 1B, the absorbent medium may swell, requiring the seal 170 to allow for expansion as swelling takes place. In this configuration, the device 100 may prevent old or contaminated sweat absorbed by medium 130 from mixing with the flow 14 of new sweat emerging from the skin 12 underneath the device 100. Furthermore, the device 100 may prevent sensing of sweat from areas of skin outside the device 100, which in many cases would be older sweat. For example, if the device 100 is placed on an individual's lower abdomen and the wearer is standing, the seal 170 may prevent the device 100 from sensing older sweat flowing down the torso from the chest and neck. In an exemplary application of device 100, the device is placed on the abdomen or forearm of a sweating individual; the device 100 could work properly to measure and report sweat biomarkers even if the user went swimming, took a shower, or other possible external contaminants were introduced. Although the seal 170 in FIG. 1B is described as being expandable or stretchable, alternate embodiments of the present invention could include a seal 170 that is not stretchable or that is rigid in mechanical form. In such an alternate embodiment, for example, a simple shape change of the seal 170 could accommodate swelling of the absorbing medium 130. In another embodiment, the absorbing medium 130 could be implemented with little or no swelling as it absorbs sweat 14. Similarly, other elements or materials used in embodiments of the present invention could be rigid in mechanical form.

Figure 2:
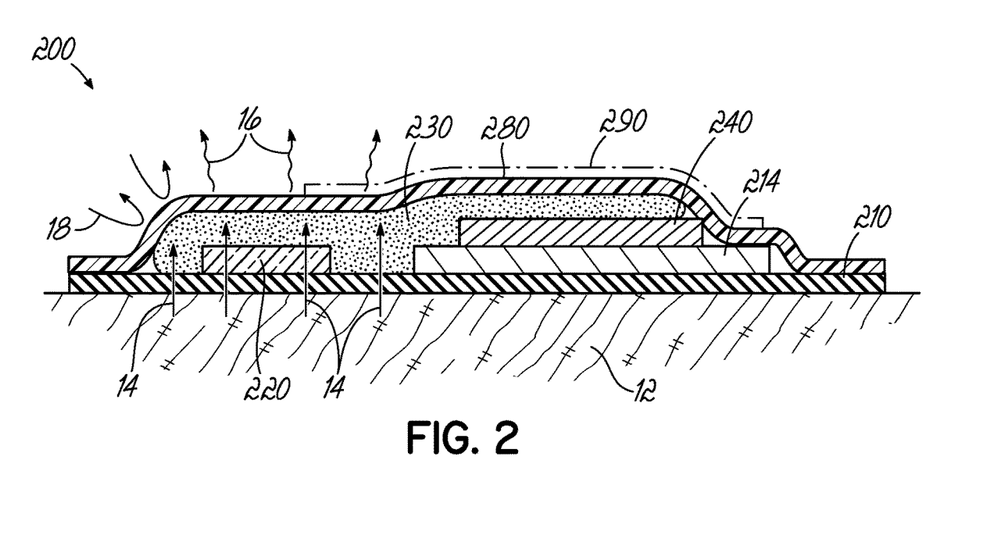
FIG. 2 is a cross-sectional view of a sealed device according to one embodiment of the present invention.

With reference to FIG. 2, the device 200 is similar in construction to the device 100 shown in FIGS. 1A and 1B, except as otherwise described below. In that regard, similar reference numerals refer to similar features shown and described in connection with FIGS. 1A and 1B. Device 200 includes a gas-permeable seal 280. By way of example, the gas-permeable seal 280 may be a selectively sealing film, membrane, textile, or other covering. Because seal 280 is permeable to gas, water vapor from sensed sweat may escape the device 200. In one embodiment, seal 280 may be a textile that is hydrophobic, which therefore repels water but which allows water vapor to escape the device 200 as indicated by arrows 16. Like seal 170, seal 280 protects the device 200 from outside contaminants, as indicated by arrows 18. This configuration allows the device 200 to be used in prolonged fashion while also sealing it from potential external fluid contamination. In this regard, device 200 may have an improved wearable duration and may be more practical to wear (e.g., by not swelling to as large a volume) as compared to device 100. Although the device 200 is shown including an absorbent medium 230, alternate embodiments may not include an absorbent medium. For example, in embodiments where the application of a device has a shorter term usage and where buildup of sweat solute concentrations around the sensor 220 would not be an issue, an absorbent medium may not be included.

With further reference to FIG. 2, in an alternate embodiment, seal 280 may also be water permeable but generally impermeable to one or more water soluble solutes (e.g. aqueous solutes), such as solutes in sweat. In one embodiment, seal 280 could be a reverse osmosis membrane. In this exemplary embodiment, water could traverse the seal 280 while external solute contaminants would be prevented from entering device 200. In an exemplary application of device 200, seal 280 could block a detergent used while a person wearing the device 200 takes a shower because a detergent could impair the function of some types of sensors or device configurations. Although water could enter the device 200 in this example, the water would not interfere with sensing of new sweat indicated by arrows 14 if the flow rate of the new sweat is adequate to provide only new sweat underneath the sensor 220.

With further reference to FIG. 2, in an alternate embodiment, seal 280 may also be a membrane that selectively transports a species, such as a certain solute in sweat. This selective transport may advantageously remove a predetermined component of sweat that may build up to an undesirable concentration in device 200. For example, seal 280 could comprise one or more of several types of ion-selective or ion-permeable membranes that are not porous to free flow of fluid or are at least suitably restrictive to flow of fluid. In one embodiment, seal 280 allows $Na^+$ to be removed from the device 200 to prevent the solute from building up to too high of concentration over time. In an advantageous aspect, such a function provided by seal 280 could prolong usage of the device 200.

With further reference to FIG. 2, in an alternate embodiment, device 200 may include an additional material or layer(s) exterior to the seal 280. In the illustrated embodiment, device 200 includes an optional refreshable collection layer 290. The collection layer 290 is configured to collect sweat and/or sweat solutes and to be refreshed of the collected sweat and/or sweat solutes where at least a portion of the collected sweat and/or sweat solutes is removed. In this regard, the collection layer 290 may be a textile, material, or surface that can be washed of some or all of the collected solutes or sweat and therefore be at least partially refreshed to collect more solutes or sweat. During the washing away of such sweat and/or sweat solutes, seal 280 also prevents substantial back-contamination of the washing fluid from reaching the contamination sensitive portions of the device 200. Therefore, in one embodiment of the present invention, the seal 280 would seal only a portion of such a device 200 allowing limited fluidic contact between collection layer 290 and absorbent medium 230. In one embodiment, collection layer 290 is an externally evaporative textile. In an advantageous aspect, the presence of a refreshable collection layer could prolong the usable lifetime of a device such as device 200. For example, a refreshable collection layer 290 would extend the usable lifetime of a device 200 in applications where high sweat rates exist during use of the device 200.

Figure 3:
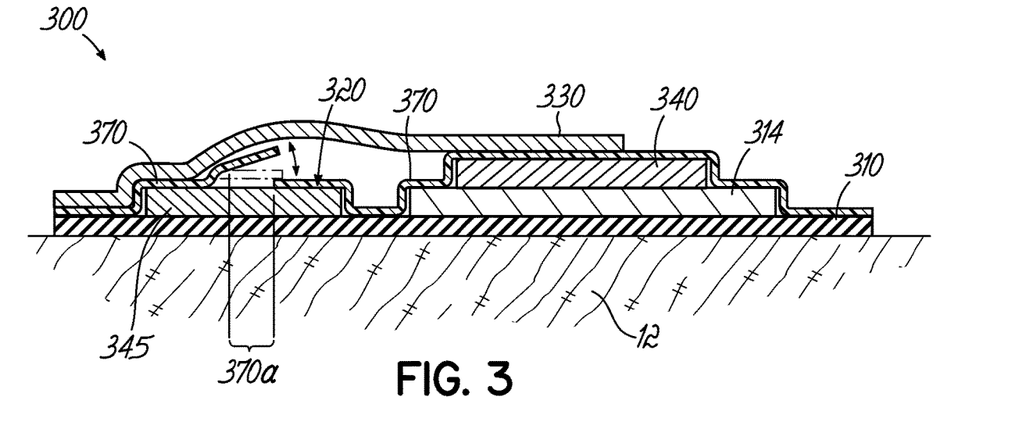
FIG. 3 is a cross-sectional view of a sealed device according to one embodiment of the present invention where a portion of the device is sealed from contamination.
Figure 3A:
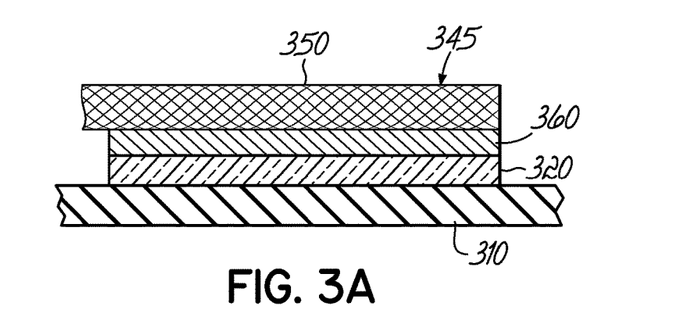
FIG. 3A is a cross-sectional view of a portion of the sealed device of FIG. 3.

With reference to FIG. 3, the device 300 includes similar features as the devices 100, 200, except as otherwise described below. In that regard, similar reference numerals refer to similar features shown and described in connection with FIGS. 1A, 1B, and 2. The device 300 includes an artificial sweat stimulation and sensing mechanism 345. In this regard, the mechanism 345 includes an iontophoresis electrode 350, a sweat stimulant 360, such as a pilocarpine gel, and a sensor 320 as shown in FIG. 3A. The sensor 320 is porous such that the sweat stimulant 360 may be administered to the skin 12 through the sensor 320 by iontophoresis to artificially stimulate sweating. With further reference to FIG. 3, the device 300 includes a layer 330 and a sweat impermeable material 370. Layer 330 may be, for example, a gel or a textile covering at least a portion of sweat impermeable material 370. With the exception of pathway 370a, sweat impermeable membrane 370 seals possible contamination-sensitive features of device 300 from fluid from an external source. In this configuration, the opening in the membrane 370, which may also be viewed as a one-way flow component, is usually in a closed position. The pathway 370a allows fluid to escape as excess sweat pressure builds up between the skin 12 and the sweat impermeable material 370. In alternate embodiments, the open position of the pathway 370a may be the default position, but these embodiments would require a mechanism to actively close the pathway 370a when there is a chance of external contaminants coming back through the valve. For example, such a mechanism may be triggered by an external moisture sensor. By way of example, the sweat impermeable material 370 may be a membrane, textile, or film. In one embodiment, material 370 is a polymer film and pathway 370a is loose flap that will open with sweat pressure but close or remain suitably constrictive to fluid flow when external fluid pressure is provided, for example by swimming, washing, or from other sweat on the body. Material 370 could utilize any substantially one-way flow mechanisms including one-way valve mechanisms known by those skilled in the art. In this configuration, the sweat stimulation and sensing mechanism 345 is covered by the sweat impermeable material 370. Protecting the mechanism 345 from outside contaminants is important because, for example, a pilocarpine source could become diluted if exposed to water while the wearer of the device is bathing or swimming. Those skilled in the art will recognize that embodiments may use a combination of aspects of the present invention.

Embodiments of the present invention may include a variety of sweat stimulation techniques. By way of example, sweat stimulation may be applied by chemical, electrical, heat, or other mechanisms. In an aspect of the present invention, an artificial sweat stimulation component can be applied externally to any sealed sensing device. In one embodiment, a sweat sensing device is applied to the skin, and sweat stimulation is applied to regions near the sensing device. In this manner, sweat is therefore provided to the sensing device by sudo-motor axon reflex sweating. Accordingly, embodiments of the present invention may not include an integrated sweat stimulation technique, which may decrease the cost, increase ergonomics, or provide some other advantage. In one embodiment where a sweat sensing device is a patch, the patch may need to be held against the skin for device security and compliance reasons, and sweat sensing may only be tested as needed, initiated by an external sweat stimulation method. Some sweat stimulating chemicals can induce sweating even several hours after the chemical is dosed into the skin. Sweat stimulation could be performed by a re-usable device that also applies a sweat sensing patch. For example, an application device could apply a sweat sensing patch to the skin while using iontophoresis to provide a dose of pilocarpine around the external edge of the patch. Those skilled in the art will recognize that other stimulation techniques external or internal to a sealed device are possible.

Figure 4:
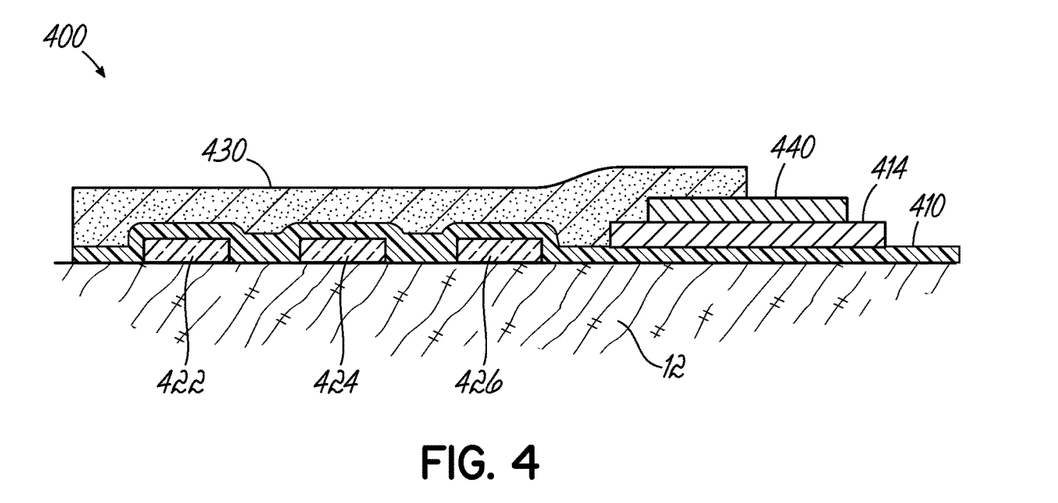
FIG. 4 is a cross-sectional view of a sealed device according to one embodiment of the present invention where the sensors are in contact with the skin.

With reference to FIG. 4, in one embodiment, a device 400 includes a plurality of sensors 422, 424, 426 in direct contact with the skin 12. Device 400 further includes an adhesive 410, an absorbent medium 430, and electronics 440 carried by a substrate 414. In this embodiment, adhesive 410 seals the sensors 422, 424, 426 against the skin 12. Depending on the application, having sensors in direct contact with the skin may be advantageous. Although not shown, device 400 may include other aspects of the present invention. Those skilled in the art will recognize that methods other than using adhesives to hold devices according to embodiments of the present invention against skin may be used, such as mechanical pressure or a strap, among other methods.

Figure 5:
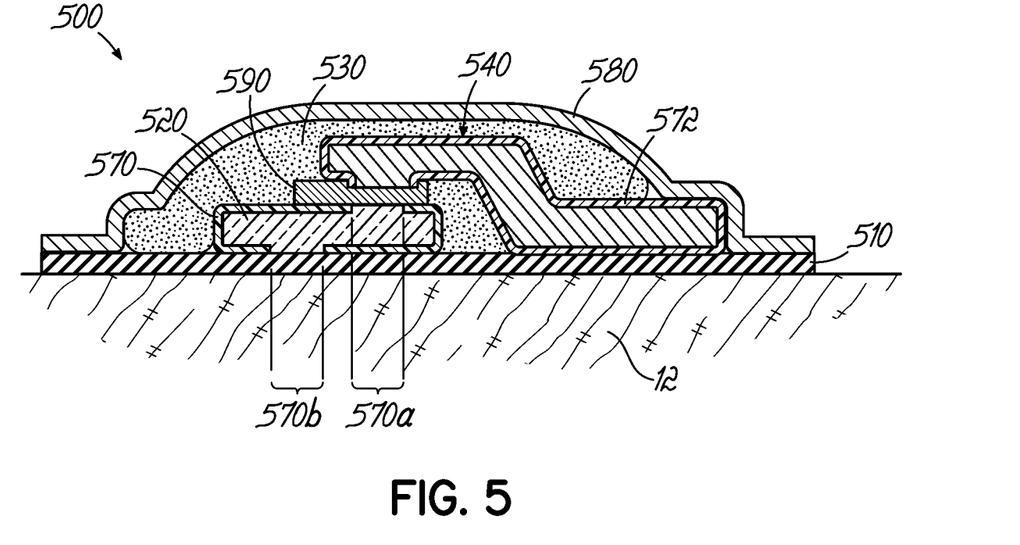
FIG. 5 is a cross-sectional view of a sealed device according to one embodiment of the present invention where a portion of the device is selectively sealed.

With reference to FIG. 5, in one embodiment, a device 500 includes a sensor 520 in electric communication with electronics 540. Device 500 is adhered to the skin 12 by an adhesive 510 and includes an absorbent medium 530. With the exception of regions 570a, 570b, the sensor 520 and electronics 540 are sealed by sweat impermeable materials 570, 572, respectively. The sweat impermeable materials 570, 572 may be, for example, a membrane, textile, coating, or film. In region 570a, the sensor 520 electrically contacts the electronics 540 through an interconnecting component 590. The component 590 provides a vertical electronic connection between the sensor 520 and the electronics 540, provides horizontal electrical insulation for the electronic connection, and provides a seal such that sweat does not come into contact with electronics 540 or any interconnection between electronics 540 and sensor 520. In this embodiment, component 590 could be a double-sided tape, or elastomeric interconnect, where the edges of the component 590 may contact sweat but do not conduct electricity in the horizontal direction therefore providing adequate electrical insulation and sealing of said electrical connection. In one embodiment of the present invention, the component 590 is a double-sided z-axis electrical tape (i.e., anisoptropically conductive tape), such as a tape manufactured by 3M Corp. For example, the 3M Anisotropic Conductive Film can, along with impermeable materials 570, 572, seal the device 500 from sweat except where it is desirable for sweat to touch the device 500, such as the side of sensor 520 facing the skin 12 as indicated by 570b. In an alternate embodiment of the present invention, the component 590 could be an elastomeric interconnect, such as a ZEBRA connector sold by Fuji Polymer Industries Co. Such a component 590 or similar components can be referred to as a hermetically sealing and electrically interconnecting component. Seal 570 allows sweat to reach the sensor 520 surface at the region 570b without electrically shorting the sensor 520 or the electric connection through the component 590. In one embodiment, material 570 is a parylene coating applied to the exposed surfaces of the sensor 520 to electrically insulate the sensor 520, except for regions 570a, 570b. In this regard, the sensor 520 may be masked during parlyene deposition by using, for example, a removable piece of adhesive tape such as Kapton tape. After removal of the tape, regions 570a, 570b of the sensor 520 are not coated by the material 570. Other sealants are possible that can be selectively placed by area, as commonly used in electronics and printed circuit boards.

Figure 6:
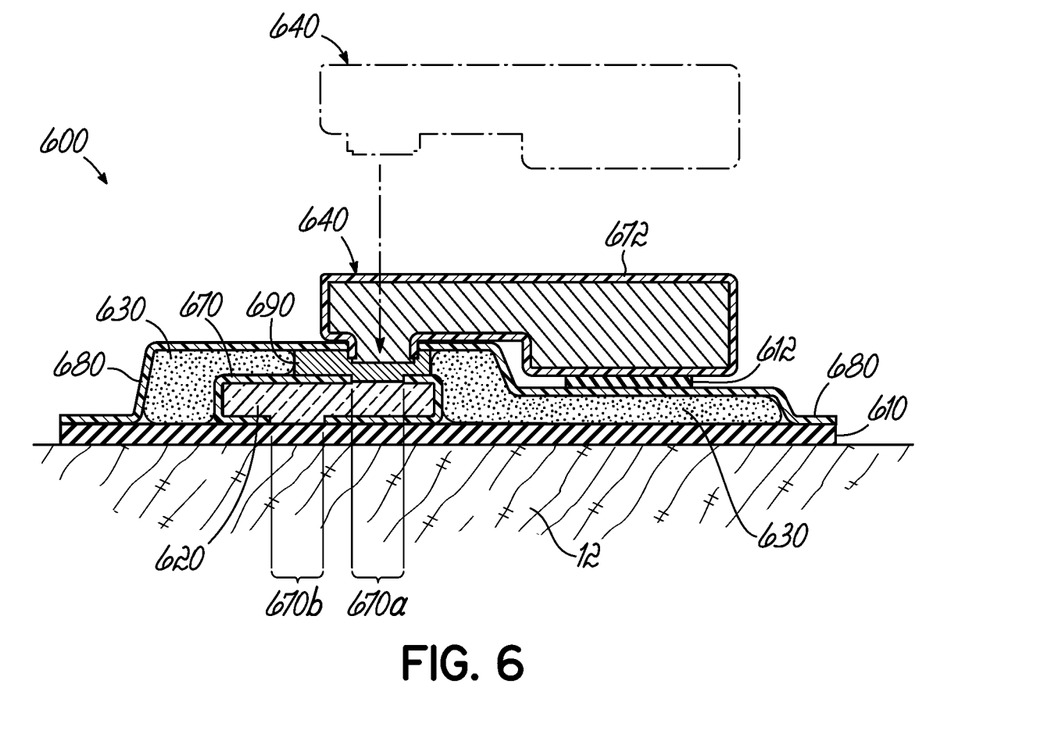
FIG. 6 is a cross-sectional view of a sealed device according to one embodiment of the present invention where the device includes a reusable portion and a disposable portion.

With reference to FIG. 6, in one embodiment, the device 600 includes similar features as the device 500, except as otherwise described below. In that regard, similar reference numerals refer to similar features shown and described in connection with FIG. 5. Device 600 includes a sensor 620 electrically connected to electronics 640 by a component 690. The sensor 620 and electronics 640 are sealed by sweat impermeable materials 670, 672, respectively. Device 600 is adhered to the skin 12 by an adhesive 610 and includes an absorbent medium 630. Seal 680 seals the device 600 against the adhesive 610 and, thus, the skin 12. Because electronics 640, which may include a battery, may be expensive, it is advantageous to configure the device 600 such that the electronics 640 may be reusable. In the illustrated embodiment, excepting electronics 640 and impermeable material 672, the remainder of the device 600 is disposable. Thus, in one aspect, one or more components of devices according to embodiments of the present invention may be disposable, refreshable, or reusable in any electrical, fluidic, chemical, or other useful manner. In one embodiment, the component 690 is a pressure sensitive adhesive that allows attachment of reusable electronics 640 and provides sealing as well. Device 600 further includes an optional adhesive 612, which aids in mechanically coupling the electronics 640 to the other components of the device 600. In one embodiment, electronics 640 could additionally include microfluidics or other lab-on-chip type features for sensing sweat or its solutes.

With further reference to FIG. 6, in alternate embodiments, the component 640 could contain both electronics and sensors or could contain no electronics at all and could be a reusable device for collecting sweat samples (e.g., contains fluidics) or a reusable device that provides other sensing methods (e.g., optical, colorimetric, or other suitable techniques) for sensing sweat or its solutes. In such embodiments, component 620 could therefore be a microfluidic sampling component, for example. Therefore, component 690 could provide a seal while also acting as an interconnecting component by providing a fluidic or microfluidic interconnection between elements 620 and 640. In this configuration, sweat could pass through component 620, through component 690 and into component 640. This again illustrates that more portions of the present invention may be disposable, refreshable, or reusable in any electrical, fluidic, chemical, or other useful manner, therefore element 690 can be more broadly referred to as a sealed and adhesive interconnect component.

In one aspect of the present invention, because many sensors and antennas (especially for RFID applications) or other electrical components are sensitive to impedance and sweat contact can change the electrical capacitance seen by such electrical components, impedance sensitive electrical components may be insulated. In one embodiment of the present invention, the impedance sensitive electrical components of a device are coated with an electrical insulator, the coating being at least 5 μm in thickness. In another embodiment, the impedance sensitive electrical components have an electrically insulating coating with a thickness of at least 50 μm. By way of example, the electrical insulator may be acrylic, silicone, or parylene. The electrical insulator minimizes any undesirable change in electrical capacitance as the device is placed adjacent to or wetted nearby by sweat.

Embodiments of the present invention may include sweat or sweat solute absorptive mediums that are reusable or refreshable. Such absorptive mediums useful in the present invention may include, for example, gels, charcoals, filters, textiles, and pouches. Using reusable or refreshable absorptive mediums may prolong usage of the device. In one embodiment, a device includes an absorbing medium that may be attached, detached, and reattached to the device. Such absorbing medium could be for example element 290 shown for device 200 in FIG. 2. Such an absorbing medium may be attached to a device using a variety of methods, such as using adhesives. Absorbing mediums may also be attached to a device using more rigid fixation methods, such as with a latch or a screw.

In one aspect of the present invention, components of a device, such as a sensor, are protected from possible contamination from the skin. Contaminants from the surface can also be thought of being 'outside contaminants' because the skin surface is outside the body and external to the sweat ducts which are the targeted source of analytes to be measured. In this regard, one or more solutes in sweat could foul the surface of, or degrade a sensor or other component. For example, oil from the skin could foul or degrade a sensor. Embodiments of the present invention may include a membrane or material that provides a seal and protects the components of the device that are susceptible to contamination. By way of example, a device may include, for example, a dialysis membrane or microfiltration membrane between newly generated sweat and the sensors. The membrane material may allow for selective solute transport between the skin and, for example, a sensor, which would narrow the range of solutes that reach the sensor. Such a sealing material with solute selective transport between the sensors and the skin could also be adhesive or be coated with an adhesive. In one embodiment, this sealing material capable of solute selective transport may be represented as element 210 as shown in FIG. 2.

In another aspect of the present invention, a device includes an oil absorbing or oleoscopic material to seal or protect the sensors, or other oil-sensitive features of the device, from oil emerging from skin. For example, commercially available Imbiber Beads or the materials used in Imbiber Beads for oil cleanup applications can be incorporated between the skin and the sensors in several ways. In one embodiment, such beads may be embedded in the adhesive material 210 of FIG. 2. In this embodiment, the beads effectively form a seal against oil, while allowing sweat to flow through the material 210. In this regard, the seal provided by adhesive 210 is selectively permeable. Any such implementation of a method of protecting devices or sensors of the present invention from skin oil can be referred to as a device having a protecting material for oil from skin.

This has been a description of the present invention along with a preferred method of practicing the present invention, however the invention itself should only be defined by the appended claims.

What is claimed is:

1. A device comprising:
   a sensor for measuring a characteristic of an analyte in a sweat sample;
   a sweat impermeable material comprising a first region configured to allow fluidic communication between the sensor and the sweat sample, wherein the sweat impermeable material is configured to partially cover said sensor, and to protect the sensor from outside contaminants when said device is placed on a device wearer's skin; and
   an external seal at least partially covering the device, wherein the external seal is configured to protect the device from outside contaminants when said device is placed on the skin.

2. The device of claim 1, further comprising:
an absorbing medium to absorb sweat from the skin, said absorbing medium being covered by said external seal.

3. The device of claim 2, wherein said external seal is expandable.

4. The device of claim 2, wherein the absorbing medium is configured to allow attachment to the device, detachment from the device, and reattachment to the device.

5. The device of claim 1, wherein said external seal is permeable to gas.

6. The device of claim 1, wherein said external seal is permeable to liquid water and impermeable to at least one solute.

7. The device of claim 1, wherein said external seal is selectively permeable to at least one aqueous solute.

8. The device of claim 1, wherein said external seal is an adhesive.

9. The device of claim 1, further comprising:
a collection layer for collecting sweat and/or sweat solutes and configured to be refreshed, wherein at least a portion of the collected sweat and/or sweat solutes is removed.

10. The device of claim 1, further comprising:
a sweat stimulator for stimulating sweat when the device is placed on the skin, wherein the sweat stimulator comprises an iontophoresis electrode and a chemical to induce sweating.

11. The device of claim 10, wherein said sweat stimulator is covered by said external seal.

12. The device of claim 10, wherein said sweat stimulator is external to said external seal.

13. The device of claim 1, wherein said sweat impermeable material includes a one-way valve configured to permit a flow of sweat from the skin to pass through and away from the sensor and for restricting a flow provided by an external source.

14. The device of claim 1, further comprising:
electronics;
an electronics seal covering the electronics, wherein the electronics seal is configured to protect the electronics from outside contaminants, and wherein said electronics seal includes a second region configured to allow electronic communication between said electronics and the sensor;
wherein said sweat impermeable material includes a third region configured to allow electronic communication between said electronics and the sensor; and
an interconnector configured to allow electronic communication between said electronics and the sensor, wherein the interconnector electronically connects the second region with the third region, and wherein the interconnector seals the second region and the third region from contacting sweat.

15. The device of claim 14, wherein said sensor is coplanar and said interconnector is configured to conduct electricity perpendicularly to said sensor.

16. The device of claim 14, wherein said electronics are configured to allow attachment to the device, detachment from the device, and reattachment to the device.

17. The device of claim 1, wherein at least one component of said device is sensitive to impedance and said component includes a coating comprising an electrical insulating material, and wherein said coating has a thickness of at least 5 μm.

18. The device of claim 1, further comprising:
a plurality of sensors for measuring a characteristic of one or more analytes in the sweat sample; and
a plurality of sweat impermeable materials, each comprising a first region configured to allow fluidic communication between one of the plurality of sensors and the sweat sample, wherein each of the plurality of sweat impermeable materials is configured to partially cover said one of the plurality of sensors, and to protect said one of the plurality of sensors from outside contaminants when said device is placed on the device wearer's skin.

* * * * *